United States Patent [19]

Pink et al.

[11] 4,370,751

[45] Jan. 25, 1983

[54] METHOD OF NON-DESTRUCTIVELY MEASURING THE PRESSURE OF A GAS IN A CLOSED VESSEL

[75] Inventors: Francis X. Pink, Norwood; Carmine Persiani, Milford; Paul Lublin, Framingham, all of Mass.

[73] Assignee: GTE Laboratories Incorporated, Waltham, Mass.

[21] Appl. No.: 223,874

[22] Filed: Jan. 9, 1981

[51] Int. Cl.³ .............................................. G01N 23/22
[52] U.S. Cl. .......................................... 378/47; 378/45
[58] Field of Search ....................... 378/47, 46, 45, 44

[56] References Cited

U.S. PATENT DOCUMENTS 2,977,473  3/1961  Hendee ................................. 378/47
3,344,273  9/1967  Ziegler ................................. 378/47

Primary Examiner—Craig E. Church
Attorney, Agent, or Firm—Fred Fisher

[57] ABSTRACT

The pressure of a gas in a closed vessel can be non-destructively read by irradiating the closed vessel with x-rays. The irradiated gases in the vessel emit x-rays characteristic of various gases within the vessel. The characteristic x-rays, which pass out of the vessel, are discriminated and their intensity count converted to a pressure reading.

7 Claims, 2 Drawing Figures

METHOD OF NON-DESTRUCTIVELY MEASURING THE PRESSURE OF A GAS IN A CLOSED VESSEL

BACKGROUND OF THE INVENTION

1. Field of the Invention

This invention relates to a method of non-destructively measuring the pressure of a gas in a closed vessel, and, in particular, to a method of non-destructively measuring the pressure of gases in glass envelopes, such as autolamps and flashbulbs. Accordingly, it is a general object of this invention to provide new and improved methods of such character.

2. Description of the Prior Art

Various prior art methods of measuring pressure of a system assume that when a gas is introduced at a particular pressure into a system, and the system is sealed-off, the gas pressure is the same as the seal-off pressure and remains constant. Disadvantageously, no provision is made for leaks either during the time of pressurization or thereafter.

In the production of high intensity halogen headlights, there is a need to constantly monitor the gas fill pressure of the lamps. Usually, such measurement is manually performed, and, therefore, is slow and expensive. Thus, it is desired to provide a rapid and, preferably, non-destructive measurement of the gas pressure. One proposed approach of monitoring the pressure is by relating the intensity of the HBr band at 3.9–4.1 $\mu$m to the increase in pressure. However, the glass used as the lamp envelope absorbs substantially in this region, thus lowering the sensitivity of the method. In addition, the content or HBr is generally only 0.2–0.3% by weight of the total gas content, leading to further error in measurement, assuming there is a signal at all. Furthermore, pressure increase causes broadening of the HBr band causing a further decrease in signal.

SUMMARY OF THE INVENTION

Another object of this invention is to provide for a new and improved method of non-destructively measuring pressure, repeatedly and in situ.

Yet another object of this invention is to provide for a new and improved method for monitoring any change in gas pressure over the life time of a sealed-off system.

Still another object of this invention is to provide for a new and improved method for rapidly evaluating large numbers of sealed-off systems wherein such method is applicable to production line quality control.

In accordance with one embodiment of the invention, a method of non-destructively measuring the pressure of a gas in a closed vessel includes irradiating the closed vessel with x-rays or any other radiative source having appropriate energy. Characteristic secondary radiation emitted by the irradiated gas within the closed vessel and emerging therefrom is measured by a solid state energy dispersive detector. The detected secondary radiation is discriminated with respect to a particular emitting element to provide an intensity signal. The signal is converted to a pressure reading. In accordance with certain features of the invention, the vessel can be a glass envelope. The vessel and its constituents can be an autolamp. The autolamp can contain a predominance of noble gas, such as krypton or xenon, together with lesser amounts of nitrogen and a halogen compound, and the detected secondary emission is discriminated with respect to the noble gas.

BRIEF DESCRIPTION OF THE DRAWING

Other objects, advantages, and features of this invention, together with its method of operation, will become more apparent from the following description, when read in conjunction with the accompanying drawing, in which.

DESCRIPTION OF A PREFERRED EMBODIMENT

The invention utilizes x-ray or gamma radiation to excite gaseous atoms and/or molecules in a closed system and recording the secondary radiation produced by the gaseous species by appropriate circuitry. The resulting signal is then related to the number of gaseous atoms and/or molecules, the volume, thickness of container, etc. and, therefore, the pressure. Specifically, gaseous species in a container are excited with primary x-rays. The secondary characteristic x-rays from the gas are of sufficient energy to penetrate the container walls and enter the detector and recorded as such. Gases whose radiation do not have sufficient energy to penetrate the container walls may be monitored by premixing a fixed proportion of a higher atomic number gas. The radiation from the latter gas would have sufficient penetration to pass through the container to be measured.

Preferably, the invention includes the excitation of the krypton fill gas in halogen lamps by polychromatic x-rays. The krypton then emits the Kr K$\alpha$ characteristic radiation. The Kr K$\alpha$ intensity is measured and related to the pressure in the envelope by reference to a previously determined standard calibrated curve.

TEST SET UP

The feasibility of the use of x-rays to monitor pressure was studied using a test set up. The primary x-rays were produced using the spot focus of a standard diffraction tube operating at 35 KV and 10 m A. The generator is operated in the constant potential mode. A special but simple holder was constructed of glass tubing such that the lamps would be held rigidly, positioned accurately yet changed with ease. A multichannel x-ray energy analyzer was used to analyze the emission data from a Si(Li) detector. This detector was chosen for its high counting efficiency in the Kr K$\alpha$ (12.631 Kv) energy region. A 400 ev. window was used to separate the Kr K$\alpha$ emission from interferring energies and background correction. A total counting time of 60 seconds was used and the resulting peak and background integrated to give the intensities of each. In each case, the background was subtracted from the line intensity to produce net intensities.

Following x-ray intensity measurements on randomly selected lamps of the 1A type, the pressure was measured destructively in each of the lamps. The method is conventional and consists of measuring the volume of the released gas at one atmosphere, measuring the volume of the lamp after gas release and calculating back to the initial pressure by Boyle's Law. The glass bulbs were then broken and wall thickness of the lamp were measured. This latter piece of data was to determine the amount of attenuation of the Kr Kα intensity through the envelope.

Figure 1:
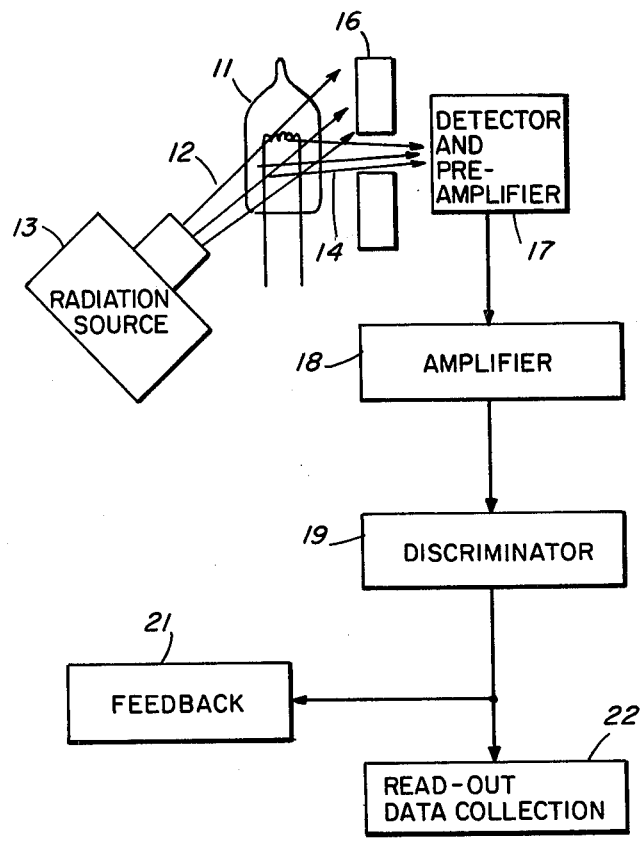
FIG. 1 is a block diagram of apparatus for carrying out the method of the invention.

Referring to FIG. 1, the sample (11), a glass envelope containing constituents for an autolamp or flashlamp such as krypton, nitrogen and a halogen compound, is bombarded with primary radiation (12) from an x-ray generator (13). The krypton represents approximately 95% of the gas composition. Secondary radiation (14) passes through a radiation shield and collimator (16) and is detected and amplified by a detector and preamplifier (17). The detected signal is further amplified by an amplifier (18) and passed to discriminator (19). The discriminator (19) selects a signal corresponding to a selected element, preferably the noble gas, krypton. Its output can be coupled to a feedback (21) for further on-line control or to a data collection (22) system.

X-RAY ABSORPTION

Since x-rays are attenuated by their passage through material, the absorption of the Kr Kα line through the type 1720 glass envelope of the lamp was considered. Using the nominal composition of the glass, the mass absorption coefficient $\mu/\rho$ for the Kr Kα was calculated to be 10.25 cm$^2$/gm. In type 1A lamps, the wall thickness specification varies from 0.034 inch to 0.040 inch. This represents a variation in the absorption of the Kr Kα from 0.092 to 0.059 respectively and corrective procedures would be necessary to allow for this absorption. However, in these experiments, the absorption effect due to wall thickness variations was minimal and corrections did not substantially affect the results.

DATA

A summation of data accumulated on pressure, wall thickness and corrected Kr Kα intensity is presented in Table 1. The Kr Kα intensity, as noted here, is corrected for both background and attenuation by wall thickness. Also presented are lamp volume and lamp wall thickness measurements.

TABLE 1

| Lamp Type | Sample No | KrKαInt. (cts) | Lamp Vol. (cc) | Lamp Press. (atoms) | Wall Thick. (cm) |
|---|---|---|---|---|---|
| 1A | 10 | 18,456 | 1.4 | 3.93 | 0.097 |
|  | 11 | 20,422 | 1.5 | 4.33 | 0.099 |
|  | 12 | 24,186 | 1.5 | 4.80 | 0.096 |
|  | 13 | 17,831 | 1.3 | 3.38 | 0.099 |
|  | 14 | 29,117 | 1.4 | 5.64 | 0.093 |
|  | 15 | 21,595 | 1.2 | 4.00 | 0.094 |

Figure 2:
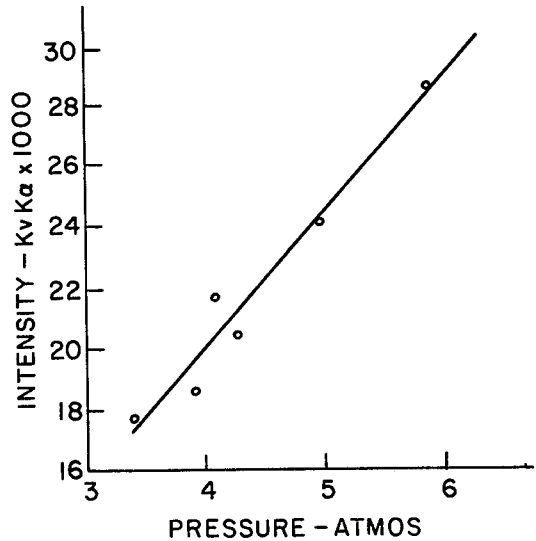
FIG. 2 is a graph of intensity of radiation versus pressure, suitable for understanding the invention.

It is readily seen that in the 1A samples there is a correlation between Kr Kα intensity and measured gas pressure. FIG. 2 demonstrates this relationship as a straight line from 3 to 6 atmospheres of pressure.

The nominal gas composition of the tungsten filament lamps is given as 5% N$_2$, 0.31% HBr and Bal. Kr. A gas analysis on a randomly chosen sample gave 6.38% N$_2$, 93.16% Kr$_2$, and 0.008% O$_2$.

CONCLUSION

The glass envelope, including the gases inside, are irradiated with x-rays. The irradiated gases, in turn, emit secondary radiation which emerge through the glass envelope, are collimated and are appropriately detected and measured. Other radiations emitted by silicon, oxygen and nitrogen are not detected because they are readily absorbed by the air path between the sample and detector.

In producing an autolamp, the glass vessel is filled from 3 to 10 atmospheres of krypton, about 3 percent nitrogen, and about 0.3 percent HBr. The high (95 percent) concentration krypton is easily detected and is proportional to the pressure. The method is non-destructive and there is no discoloration of the glass from the radiation.

The invention is believed most useful when the emitted radiation is from 0.3 to 2.0 A° in wavelength. Such span includes elements which range from iron to uranium in the periodic table.

What is claimed is:

1. A method of non-destructively measuring the pressure of a gas in a closed vessel comprising
   irradiating said closed vessel with x-rays;
   detecting secondary radiation emitted by irradiated gas within and emerging from said closed vessel;
   discriminating the detected secondary radiation with respect to a particular element to provide an intensity count; and
   converting said count to a pressure reading.

2. The method as recited in claim 1 wherein said vessel is a glass envelope.

3. The method as recited in claim 1 wherein said closed vessel and its internal constituents form an autolamp.

4. A method of non-destructively measuring the pressure of the gases within the glass envelope of an autolamp containing a predominance of noble gas, and lesser amounts of nitrogen and a halogen compound comprising
   irradiating said glass envelope with x-rays;
   detecting secondary radiation emitted by irradiated gas within said envelope;
   discriminating the detected secondary radiation with respect to said noble gas to provide an intensity count; and
   converting said count to a pressure reading.

5. The method as recited in claim 4 wherein said noble gas is krypton.

6. The method as recited in claim 4 wherein said noble gas is xenon.

7. A method of non-destructively measuring the pressure of the gases within the glass envelope of an autolamp containing krypton, nitrogen, and a halogen compound comprising
   irradiating said glass envelope with an x-ray source;
   detecting secondary radiation emitted by irradiated gas within said envelope without the detection of primary radiation from said source;
   discriminating the detected secondary radiation with respect to krypton to provide an intensity count; and
   converting said count to a pressure reading.

* * * * *